United States Patent [19]

Gal et al.

[11] 4,039,388

[45] Aug. 2, 1977

[54] DIAGNOSTIC TEST FOR NIEMANN-PICK DISEASE

[75] Inventors: Andrew E. Gal, Vienna, Va.; Roscoe O. Brady, Bethesda, Md.

[73] Assignee: The United States of America as represented by the Government, Washington, D.C.

[21] Appl. No.: 692,913

[22] Filed: June 4, 1976

[51] Int. Cl.$^2$ .......................................... G01N 31/14
[52] U.S. Cl. ............................ 195/103.5 R; 195/99; 260/403; 260/404.5; 260/606.5 P; 260/621 N; 424/7
[58] Field of Search .............. 195/103.5 R, 99; 424/7; 260/558 A, 606.5 P, 621 N, 403, 404.5

[56] References Cited

PUBLICATIONS

Gal et al., A Practical Chromogenic Procedure for the Detection of Homozygotes and Heterozygons Carriers of Niemann-Pick Disease, The New England Journal of Medicine, vol. 293, No. 13, 1975, (pp. 632–636).
Brady, R. O., Hereditary Diseases–Causes, Cures, and Problems, Angem. Chem. Internat. Edit. vol. 12, No. 1, 1973, (pp. 1–11).

*Primary Examiner*—David M. Naff

[57] ABSTRACT

An artificial substrate consisting of a 2-alkanoylamino-4-nitrophenyl phosphorylcholine hydroxide is used for determining the sphingomyelinase activity in an extract of human cells or tissues by incubating the substrate together with the extract, whereby sphingomyelinase-catalyzed hydrolysis of the substrate into the corresponding 2-alkanoylamino-4-nitrophenol and phosphorylcholine takes place in an amount proportional to the sphingomyelinase activity in the extract. Alkalinization of the 2-alkanoylamino-4-nitrophenol thereby produced to convert it into the alkali salt results in the development of a bright yellow color whose intensity is proportional to the amount of the substrate that has been hydrolyzed. Measurement of the intensity of the yellow color, for example, by means of a simple colorimeter or photometer, provides an accurate indication of the sphingomyelinase activity in the extract.

11 Claims, No Drawings

DIAGNOSTIC TEST FOR NIEMANN-PICK DISEASE

BACKGROUND OF THE INVENTION

This invention relates to novel 2-alkanoylamino-4-nitrophenyl phosphorylcholine-hydroxide compounds, and, more particularly, to their use as sphingomyelinase-specific chromogenic artificial substrates in the diagnostic testing for Niemann-Pick disease.

In patients with the hereditary disorder known as Niemann-Pick disease, excessive quantitities of the naturally occurring lipid, sphingomyelin, accumulate in certain organs and tissues, due to a deficiency of sphingomyelinase, a component enzyme of all normal mammalian tissues which catalyzes the hydrolysis of sphingomyelin into its component parts, i.e., ceramide and phosphorylcholine. Measurement of sphingomyelinase activity in extracts of human cells or tissues is a proven procedure for the diagnosis of Niemann-Pick disease, the detection of healthy heterozygous carriers of the Niemann-Pick trait, and the prenatal diagnosis of fetuses afflicted with Niemann-Pick disease. Such determination of sphingomyelinase activity has previously required the use of radioactively labeled sphingomyelin, which is difficult to prepare, expensive, and available in only very limited quantities. Moreover, most clinical laboratories are not equipped to carry out assays with the radioactive sphingomyelin, and thus such testing has been restricted to research laboratories with radioactive counting facilities.

Due to the above-described limitations of the radioactive sphingomyelin, a more practical sphingomyelinase-specific artificial substrate for use in the diagnostic testing for Niemann-Pick disease has been sought for some time. A hypothetical artificial substrate potentially useful for this purpose, consisting of 2-alkanoylamino-4-nitrophenyl phosphorylcholine compounds, was proposed a few years ago by Dr. Roscoe O. Brady, one of the present co-inventors. Such compounds chemically and structurally resemble sphingomyelin, differing therefrom only by having an aromatic ring instead of a long aliphatic chain and a nitro group replacing the primary hydroxyl one carbon removed. Dr. Brady's proposal, first published in an article by Brady et al appearing in The American Journal of Medicine, Volume 51, October 1971, Pages 423–431, was based on the supposition that sphingomyelinase in a test preparation would catalyze the hydrolysis of the proposed substrate into phosphorylcholine and a 2-alkanoylamino-4-nitrophenol, and that the latter product, upon being alkalinized, would develop a yellow color proportional in intensity to the sphingomyelinase activity in the test preparation. The 1971 Brady et al. article indicated that the synthesis of the proposed substrate from a 2-amino-4-nitrophenol starting material, and an examination of its reliability in the diagnostic testing for Niemann-Pick disease, were at that time being undertaken.

As it subsequently turned out, however, Dr. Brady's proposed artificial substrate remained merely a hypothetical substance, and its conjectured usefulness for the determination of sphingomyelinase activity remained unsubstantiated, for quite some time following the 1971 Brady et al. article, as evidenced by several subsequently published articles authored by Dr. Brady appearing in Angew. Chem. Internat. Edit., Volume 12, No. 1, January 1973, Pages 1–11; "Lysosomes and Storage Diseases", Academic Press, Inc., New York and London (1973), Pages 439–452; and "Clinical Biochemistry Principles and Methods", Walter de Gruyter, New York and Berlin, (1974), Pages 1282–1284. All of these publications indicated that Dr. Brady's proposed artificial substrate had yet to be synthesized and examined for its reliability as an indicator of sphingomyelinase activity. The fact of the matter is that even though the 1971 Brady et al article even went so far as to suggest a starting material from which the proposed artificial substrate could be synthesized, the determination of the intermediate steps required to effect such synthesis presented a substantial amount of difficulty which led to numerous unsuccessful attempts at producing the desired end product. The complete failure that was experienced in being able in any way to effect a synthesis of Dr. Brady's proposed artificial substrate, thus left this substrate remaining as merely a hypothetical substance whose utility as a reliable chromogenic indicator of sphingomyelinase activity in the diagnostic testing for Niemann-Pick disease was still a matter of pure conjecture and incapable of being actually determined.

SUMMARY OF THE INVENTION

It is accordingly a primary object of the present invention to provide a sphingomyelinase-specific artificial substrate which can be reliably utilized for the determination of sphingomyelinase activity in an extract of human cells or tissues.

Another object of the invention is to provide a sphingomyelinase-specific artificial substrate in accordance with the preceding object, which is capable of being used in a practical chromogenic diagnostic test for Niemann-Pick disease.

A further object of the invention is to provide a sphingomyelinase-specific chromogenic artificial substrate in accordance with the preceding objects, which is capable of being readily and economically synthesized.

Still another object of the invention is to provide a practical chromogenic diagnostic test procedure for determining the sphingomyelinase activity in an extract of human cells or tissues for use in the diagnosis of homozygotes and detection of heterozygous carriers of Niemann-Pick disease.

A still further object of the invention is to provide a chromogenic diagnostic test procedure in accordance with the preceding object, which is capable of being rapidly and economically carried out with the aid of equipment readily available in most clinical laboratories and not requiring sophisticated radioactive counting facilities.

The above and other objects are achieved in accordance with the present invention by providing a sphingomyelinase-specific chromogenic artificial substrate consisting of a 2-alkanoylamino-4-nitrophenyl phosphorylcholine-hydroxide having the formula

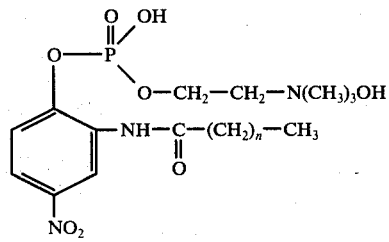

wherein $n$ is an integer from 10–18, inclusive.

The sphingomyelinase-specific chromogenic artificial substrate defined by Formula I is utilized in accordance with the present invention in a relatively simple chromogenic diagnostic test for Niemann-Pick disease by determination of the sphingomyelinase activity in an extract of human cells or tissues. Such diagnostic procedure is carried out by first forming an aqueous incubation mixture of the extract and the substrate and incubating the mixture for a determinate time period, whereby sphingomyelinase-catalyzed hydrolysis of the substrate into the corresponding 2-alkanoylamino-4-nitrophenol and phosphorylcholine takes place in an amount proportional to the sphingomyelinase activity in the extract. The mixture is then alkalinized so as to convert all of the 2-alkanoylamino-4-nitrophenol resulting from the hydrolysis into the alkali salt thereof, the alkali salt imparting to the mixture a bright yellow color whose intensity is proportional to the amount of the substrate that has been hydrolyzed. The entire protein content of the extract is then precipitated and removed from the mixture, and measured. The clear supernatant solution remaining after removal from the mixture of the protein content, retains the color developed during the alkalinization step, and measurement of the optical density of this clear supernatant solution, for example, by means of a simple colorimeter or photometer, provides a quantitative determination of the amount of the substrate that has been hydrolyzed. The sphingomyelinase activity in the extract may then be determined as the number of nanomoles of the substrate that has been hydrolyzed per hour of the incubation time period per milligram of protein in the extract.

The determination of sphingomyelinase activity by the above-described chromogenic diagnostic procedure provides a practical and reliable technique for the diagonsis of homozygotes of Niemann-Pick disease, the detection of healthy heterozygous carriers of the Niemann-Pick trait, and the prenatal diagnosis of fetuses afflicted with Niemann-Pick disease.

DESCRIPTION OF PREFERRED EMBODIMENTS

The 2-alkanoylamino-4-nitrophenyl phosphorylcholine-hydroxide compounds of Formula I which are utilized as sphingomyelinase-specific chromogenic artificial substrates for the determination of sphingomyelinase activity in accordance with the present invention, may be readily synthesized by a procedure forming the subject matter of a separate, commonly assigned, sole application of Gal (one of the present co-inventors), application Ser. No. 692,915 filed June 4, 1976, entitled "Synthesis of 2-Alkanoylamino-4-Nitrophenyl Phosphorylcholine-Hydroxide". The specific details of the synthesis procedure which are described in said Gal application are incorporated herein by reference.

Briefly, the Gal procedure for synthesizing the 2-alkanoylamino-4-nitrophenyl phosphorylcholine-hydroxide compounds of Formula I comprises first reacting 2-amino-4-nitrophenol with a $C_{12}$-$C_{20}$ alkanoyl halide to form a 2'-hydroxy-5'-nitroalkananilide having the formula (II)

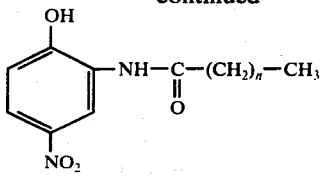

wherein $n$ is an integer from 10–18, inclusive. The compound of Formula II is then alkalinized to form the alkali phenolate salt thereof, which is then phosphorylated with $\beta$-bromoethylphosphoryl dichloride. Admixing of the phosphorylation reaction products with water results in the formation in the reaction mixture of a precipitate composed primarily of a mono-alkananilide phosphoric acid ester having the formula (III)

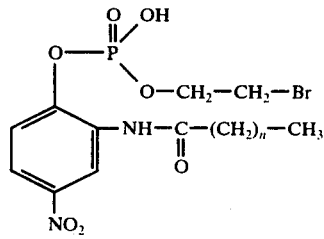

while the reaction mixture mother liquor contains dissolved therein a di-alkananilide phosphoric acid ester having the formula (IV)

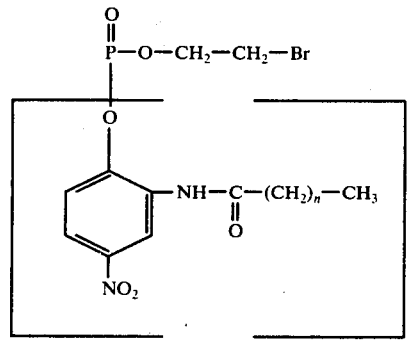

wherein $n$ has the meaning as defined above. After separating the precipitate from the mother liquor, the mono-alkananilide phosphoric acid ester of Formula III is extracted from the precipitate with sodium acetate buffer (pH 5.0). Optionally, additional amounts of the mono-alkananilide phosphoric acid ester of Formula III may be recovered from the mother liquor by cooling the mother liquor to about 4° C to thereby precipitate the di-alkananilide phosphoric acid ester of Formula IV; hydrolyzing the di-alkananilide phosphoric acid ester with alkali to thereby convert it into the form of the mono-alkananilide phosphoric acid ester of Formula III; and extracting the mono-alkananilide phosphoric acid ester resulting from the hydrolysis with sodium acetate buffer (pH 5.0). The mono-alkananilide phosphoric acid ester is then quaternized with trimethylamine to form a quaternary salt consisting of a 2-alkanoylamino-4-nitrophenyl phosphorylcholine-bromide trimethylamine salt, which is then treated with a mixture of weak acidic and weak basic ion exchange resins to thereby covert it into the 2-alkanoylamino-4-nitrophenyl phosphorylcholine-hydroxide compound of Formula I.

The preferred sphingomyelinase-specific chromogenic artificial substrate for use in the chromogenic diagnostic procedure in accordance with the present invention, is 2-hexadecanoylamino-4-nitrophenyl phosphorylcholine-hydroxide, i.e., the compound of Formula I wherein $n$ is 14. The synthesis of this preferred substrate may be effected by the above-described Gal synthesis procedure, employing palmitoyl chloride as the $C_{12}$–$C_{20}$ alkanoyl halide reacted with 2-amino-4-nitrophenol in the first step of the synthesis procedure.

The normally sphingomyelinase-contaning extracts of human cells or tissues to be employed in carrying out the chromogenic diagnostic procedure in accordance with the present invention, are those conventionally employed in the diagnostic testing for Niemann-Pick disease with the prior art radioactive sphingomyelin substrate, including extracts of human liver tissue, cultured skin fibroblasts, cultured amniotic cells, and washed leukocyte preparations. These extracts are prepared for use in the diagnostic test procedure by methods well known in the art.

In carrying out the diagnostic test procedure in accordance with the present invention, an aqueous incubation mixture of the extract and the 2-alkanoylamino-4-nitrophenyl phosphorylcholine-hydroxide substrate is first formed. Since optimal pH for sphingomyelinase activity is 5.6, the incubation mixture also preferably contains a buffering agent, such as sodium acetate buffer, to maintain the pH at this optimal value. Since it has been determined that the amount of substrate hydrolyzed by the spingomyelinase present in the extract will be proportional to the protein content of the extract over a range of from 0 to 268 micrograms, the amount of extract present in the incubation mixture should preferably by such as to be equivalent to up to 268 micrograms of protein. The initial concentration of the substrate in the incubation mixture should be such as to provide a maximal velocity of the hydrolysis reaction. In the case of the preferred substrate in accordance with the present invention, i.e., 2-hexadecanoylamino-4-nitrophenyl phosphorylcholine-hydroxide, the initial concentration for maximal velocity of the hydrolysis reaction has been found to be 14.2 millimolar.

The incubation mixture is then incubated for a determinate time period, generally from 1 to 2 hours at 37° C, it having been determined that the hydrolysis reaction is linear over a period of 2 hours. During the incubation period, sphingomyelinasecatalyzed hydrolysis of the substrate into the corresponding 2-alkanoylamino-4-nitrophenol and phosphorylcholine will take place in an amount proportional to the sphingomyelinase activity in the extract. This hydrolysis reaction is highly specific to sphingomyelinase, and will not be catalyzed by any of the other enzymes normally present in the extract. Thus, in the normal case the extract will have a high level of sphingomyelinase activity, and hydrolysis of the substrate will take place to a relatively high degree. On the other hand, if the extract contains no sphingomyelinase activity at all, which is typically the case when the extract is obtained from a patient who is a homozygote of Niemann-Pick disease Type A, no such hydrolysis will occur and the substrate will remain unchanged in the incubation mixture. Extracts obtained from patients who are healthy heterozygous carriers of the Niemann-Pick genetic trait (Type A) or who are homozygotes of Niemann-Pick disease Type C, have an intermediate level of sphingomyelinase activity within the range of between about 41 and 66 percent of normal, whereas extracts obtained from patients with Niemann-Pick disease Type B have a low level of sphingomyelinase activity within the range of between about 5 and 8 percent of normal, and hydrolysis of the substrate by such extracts will take place to a corresponding intermediate or low degree.

At the end of the incubation period, in order to chromogenically determine the amount of the substrate that has been hydrolyzed, it is necessary to alkalinize the incubation mixture, for example, with sodium hydroxide or potassium hydroxide, so as to convert all of the 2-alkanoylamino-4-nitrophenol formed during the incubation period into the alkali salt thereof. Such alkalinization is preferably effected by adding to the incubation mixture a glycine-buffered sodium hydroxide solution having a pH of 10.5, whereby the alkali salt will be the sodium salt. The alkali salt imparts to the mixture a bright yellow color whose intensity is proportional to the amount of the substrate that has been hydrolyzed.

Following the alkalinization step, the entire protein content of the extract is precipitated, for example, by adding ethanol to the alkalinized mixture, and the resulting suspension is then subjected to centrifugation so as to remove the protein content of the extract from the mixture. This protein content is then measured by methods well known in the art, for example, by the method of Lowry et al (J. Biol. Chem., Volume 193, Pages 265–275, 1951).

The clear supernatant solution remaining after the precipitation and removal of the protein content of the extract from the alkalinized mixture will have the color developed by the alkanization step. Measurement of the optical density of this clear supernatant solution by methods well known in the art, for example, with the aid of a simple colorimeter or photometer, provides a quantitative determination, after suitable calibrations have been made, of the amount of the substrate that has been hydrolyzed. For example, when the substrate employed is 2-hexadecanoylamino-4-nitrophenyl phosphorylcholine-hydroxide, the 2-alkanoylamino-4-nitrophenol hydrolysis product will be 2-hexadecanoylamino-4-nitrophenol, the sodium salt of which has a bright yellow color with an absorbance maximum at 410nm. Hence, when this substrate is employed, the measurement of the optical density of the clear supernatant solution is preferably carried out at 410nm. Under these conditions, one nanomole of the sodium salt of 2-hexadecanoylamino-4-nitrophenol has an absorbance of 0.0124.

As indicated hereinabove, the amount of substrate hydrolyzed is proportional both with respect to the time, being linear over a period of two hours, and with respect to the protein content of the extract, being linear over a range of from 0 to 268 micrograms of protein. Thus, once quantitative measurments have been made of the amount of the substrate that has been hydrolyzed and the amount of protein contained in the extract, the sphingomyelinase activity in the extract may be determined in units defined as the number of nanomoles of the substrate that has been hydrolyzed per hour of the incubation time period per milligram of protein in the extract.

The actual sphingomyelinase activity values obtained in the above-described manner in assays of cell or tissue extracts obtained from normal persons, may vary over a rather wide range depending upon such factors as the particular cell or tissue source of the extract and the conditions under which the extract is prepared for the assay. For example, typical normal sphingomyelinase activity values in extracts of cultured skin fibroblasts and cultured amniotic cells could vary anywhere from about 90 to 400, depending upon the conditions under which the culture is grown. Likewise, typical normal sphingomyelinase activity values in extracts of human tissue could vary anywhere from about 30 to about 80, whereas normal extracts of peripheral leukocytes would typically provide values in the 2-4 range.

When the diagnostic test procedure of the present invention is used in the diagnosis of homozygotes of Niemann-Pick disease Type A, cell or tissue extracts obtained from such patients typically contain no sphingomyelinase activity at all, resulting in none of the substrate being hydrolyzed and thus a sphingomyelinase activity value of 0. In such case, the above-described wide variation in normal sphingomyelinase activity values does not become a factor in obtaining a reliable diagnosis. On the other hand, it does become necessary to take this variation into account when diagnosing homozygotes of Niemann-Pick disease Type C or Type B, or when detecting healthy heterozygous carriers of the Niemann-Pick genetic trait (Type A), wherein a positive indication is provided by a sphingomyelinase activity value constituting a certain percent of normal. For example, extracts obtained from patients who are healthy heterozygous carriers of the Niemann-Pick genetic trait (Type A) or who are homozygotes of Niemann-Pick disease Type C, will have an intermediate sphingomyelinase activity value within the range of between about 41 and 66 percent of normal, whereas extracts obtained from patients with Niemann-Pick disease Type B will have a low sphingomyelinase activity value within the range of between about 4 and 8 percent of normal. In order for the test to be reliable in these cases, it is therefore necessary to effect a comparison between the sphingomyelinase activity value of the test extract and that of a normal control extract obtained from the same type of cell or tissue source and prepared for assay in the same laboratory under the identical conditions.

It should be noted that the sphingomyelinase activity values for Niemann-Pick disease Type C homozygotes are in the same range as those for Niemann-Pick disease Type A heterozygotes. However, this overlap does not preclude the usefulness of the diagnostic procedure for carrying out each of these two types of tests, since the circumstances under which the extracts to be examined are obtained and the clinical picture of the two types of patients are entirely different.

The invention is further illustrated by way of the following examples.

EXAMPLE 1 a. Extracts of human cells or tissues for use in the diagnostic test procedure described below, were prepared as follows.

Extracts of human liver tissue were prepared by mincing specimens of chilled liver tissue and suspending them in 4 volumes (w/v) of a solution of 0.02M sodium phosphate buffer pH 6.0 containing 2mg of isooctylphenoxypolyoxyethanol and 10mg of sodium taurocholate. The tissue was disrupted by hand in an allglass homogenizer. The homogenate was centrifuged at 3,000 $\times$ g for 30 minutes, and the resulting supernatant solution was used as the extract.

Extracts of cultured human skin fibroblasts and of cultured amniotic cells, were prepared by harvesting the respective cells, washing them with 5 volumes (w/v) of isotonic sodium chloride solution, and then sedimenting them by centrifugation at 1,000 $\times$ g for 10 minutes. The supernatant fluid was decanted. The pelleted cells were suspended in 4 volumes (w/v) of a solution of 0.02 M sodium phosphate buffer, pH 6.0, containing 2mg of isooctylphenoxypolyoxyethanol and 10mg of sodium taurocholate. The suspended cells were sonicated in an ice-water bath for two ten second periods with a thirty-second interval between oscillations. The mixtures were centrifuged at 25,000 $\times$ g for 20 minutes, and the resultant clear supernatant solution was used as the extract.

b. The extracts of human cells or tissues listed in Table 1, below, were each subjected to the following test procedure. An incubation mixture was first formed containing the extract, 25 $\mu$moles of sodium acetate buffer (pH 5.6), 1.5 $\mu$moles of 2-hexadecanoylamino-4-nitrophenyl phosphorylcholinehydroxide, and water in a final volume of 0.105ml. After incubating the mixture for one to two hours at 37° C, 0.4ml of a solution containing 0.1 M glycine and 0.1 M sodium hydroxide (pH 10.5) was added to alkalinize the mixture. The mixture was then swirled and then 0.7ml of absolute ethanol was added to precipitate protein, and the suspension was centrifuged at 2,000 $\times$ g for 10 minutes. The precipitated protein was removed and measured by the method of Lowry et al, supra. The optical density of the clear supernatant solution remaining after removal of the precipitated protein was measured at 410nm. Under these conditions, one nanomole of the sodium salt of 2-hexadecanoylamino-4-nitrophenol has an absorbance of 0.0124, whereby the amount of the 2-hexadecanoylamino-4-nitrophenyl phosphorylcholinehydroxide substrate that was hydrolyzed into 2-hexadecanoylamino-4-nitrophenol was quantitatively determined. The sphingomyelinase activity in the extract was then determined as the number of nanomoles of the substrate that was hydrolyzed per hour of the incubation time period per milligram of protein in the extract.

The sphingomyelinase activity values which were obtained for each of the extracts tested are listed in Table 1, below.

TABLE 1

| TYPE OF EXTRACT | DIAGNOSIS | SPHINGOMYELINASE ACTIVITY |
|---|---|---|
| Human liver tissue | Normal control | 78 |
|  | Niemann-Pick disease (Type A) homozygote | 0 |
| Cultured-human skin fibroblasts | Normal control (average of 5 cultures) | 241 |
|  | Niemann-Pick disease (Type A) homozygote | 0 |
|  | Niemann-Pick disease (Type C) homozygote | 102 |
|  | Niemann-Pick disease (Type A) heterozygote | 115 |
| Cultured amniotic cells | Normal control | 163 |
|  | Niemann-Pick disease (Type A) heterozygote | 67 |

The above-described test results clearly indicate that the chromogenic diagnostic procedure of the present invention provides a practical and reliable technique for the diagnosis of homozygotes of Niemann-Pick disease, the detection of healthy heterozygous carriers of the Niemann-Pick trait, and the prenatal diagnosis of fetuses afflicted with Niemann-Pick disease.

The embodiments of the invention in which an exclusive property or privilege is claimed are defined as follows:

1. A chromogenic method for determining the sphingomyelinase activity in an extract of human cells or tissues for use in the diagnostic testing for Niemann-Pick disease, comprising the steps of:
  a. forming an aqueous incubation mixture of said extract and a sphingomyelinase-specific chromogenic artificial substrate consisting of a 2-alkanoylamino-4-nitrophenyl phosphorylcholinehydroxide having the formula

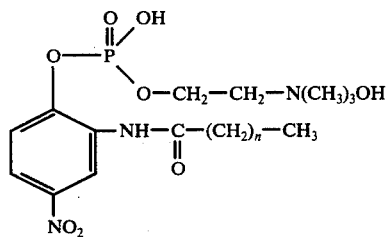

wherein $n$ is an integer from 10 to 18, inclusive;
  b. incubating said mixture for a determinate time period, whereby sphingomyelinase-catalyzed hydrolysis of said substrate into the corresponding 2-alkanoylamino-4-nitrophenol and phosphorylcholine takes place in an amount proportional to the sphingomelinase activity in said extract;
  c. alkalinizing said mixture so as to convert all of said 2-alkanoylamino-4-nitrophenol formed in step (b) into the alkali salt thereof, said alkali salt imparting to said mixture a bright yellow color whose intensity is proportional to the amount of said substrate that has been hydrolyzed;
  d. precipitating and removing from said mixture the entire protein content in said mixture, thereby leaving a clear supernatant solution having the color developed in step (c);
  e. measuring said protein content which was removed from said mixture in step (d); and
  f. measuring the optical density of said clear supernatant solution to thereby quantitatively determine the amount of said substrate that has been hydrolyzed;

whereby the sphingomyelinase activity in said extract may be determined as the number of nanomoles of said substrate that has been hydrolyzed per hour of said incubation time period per milligram of protein as measured in step (e).

2. The method of claim 1, wherein said incubation mixture is maintained at a pH of 5.6 with sodium acetate buffer.

3. The method of claim 1, wherein said extract of human cells or tissue is present in said incubation mixture in an amount equivalent to up to 268 micrograms of protein based on the protein content as measured in step (e).

4. The method of claim 1, wherein the incubation of said incubation mixture is carried out at 37° C for a period of from 1 to 2 hours.

5. The method of claim 1, wherein the alkalinization of said mixture is effected by the addition thereto of a glycinebuffered sodium hydroxide solution having a pH of 10.5, whereby said alkali salt is the sodium salt.

6. The method of claim 1, wherein the precipitation and removal of the protein content in said mixture is effected by adding ethanol to the alkalinized mixture and subjecting the resulting suspension to centrifugation.

7. The method of claim 1, wherein said substrate is 2-hexadecanoylamino-4-nitrophenyl phosphorylcholine-hydroxide.

8. The method of claim 7, wherein the initial concentration of 2-hexadecanoylamino-4-nitrophenyl phosphorylcholine-hydroxide in said incubation mixture is 14.2 millimolar.

9. The method of claim 7, wherein the measurement of the optical density of said clear supernatant solution is carried out at 410 nm.

10. A sphingomyelinase-specific chromogenic artificial substrate for use in the diagnostic testing for Niemann-Pick disease by determination of the sphingomyelinase activity in extracts of human cells or tissues, said substrate consisting of a 2-alkanoylamino-4-nitrophenyl phosphorylcholine-hydroxide having the formula

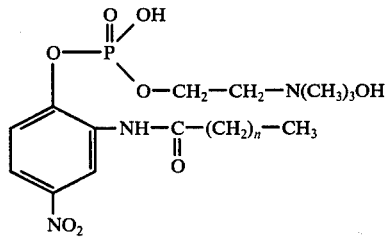

wherein $n$ is an integer from 10 to 18, inclusive.

11. the sphingomyelinase-specific chromogenic artificial substrate of claim 10, consisting of 2-hexadecanoylamino-4-nitrophenyl phosphorylcholine-hydroxide.

* * * * *